United States Patent
Pan

(10) Patent No.: US 10,101,279 B2
(45) Date of Patent: *Oct. 16, 2018

(54) METHOD OF DIAMOND COLOR GRADING

(71) Applicant: Dong-Shyogn Pan, Taipei (TW)

(72) Inventor: Dong-Shyogn Pan, Taipei (TW)

( * ) Notice: Subject to any disclaimer, the term of this patent is extended or adjusted under 35 U.S.C. 154(b) by 123 days.

This patent is subject to a terminal disclaimer.

(21) Appl. No.: 15/083,308

(22) Filed: Mar. 29, 2016

(65) Prior Publication Data

US 2018/0031487 A1 Feb. 1, 2018

(51) Int. Cl.
*G01J 3/44* (2006.01)
*G01N 21/87* (2006.01)
*G01N 21/65* (2006.01)
*G01N 21/25* (2006.01)

(52) U.S. Cl.
CPC .......... *G01N 21/87* (2013.01); *G01N 21/251* (2013.01); *G01N 21/65* (2013.01); *G01N 2201/06113* (2013.01); *G01N 2201/10* (2013.01); *G01N 2201/12* (2013.01)

(58) Field of Classification Search
CPC ........ G01N 21/87; G01N 21/65; G01N 21/25; G01N 21/658; G01N 2021/656; G01J 3/02; G01J 3/44
See application file for complete search history.

(56) References Cited

U.S. PATENT DOCUMENTS

2016/0109374 A1* 4/2016 Pan .................. G01N 21/87
356/30

* cited by examiner

*Primary Examiner* — Abdullahi Nur

(57) ABSTRACT

A non-destructive and rapid examination method is proposed for the color-grading of diamonds. A characteristic Raman peak of diamond, after being properly processed, can be used for this purpose. This novel method can be applied to color-grading of diamonds of both loose and mounted ones with satisfactory results.

1 Claim, 4 Drawing Sheets

METHOD OF DIAMOND COLOR GRADING

BACKGROUND OF THE INVENTION

1. Field of the Invention

The present invention relates to a method of diamond color grading, and particularly to a method of diamond color grading by a Raman spectrometer.

2. Related Art

According to the grading scheme of the Gemological Institute of America (GIA), "white" diamonds are classified into 23 grades, ranging from colorless (D) to pale yellow (Z). The exact color grade of a diamond significantly affects its quality and price. A traditional method of evaluating color grade is carried out by comparing the color of the sample to a set of reference stones. This traditional grading method is much more dependent on the distinguishing capabilities of individual's eyes. Also, it is inconvenient or unsuitable for the grading of inlaid diamonds. Therefore, it is a pressing issue that the existing technical problems as mentioned above are needed to be solved by providing a creative and innovative method for the purpose of grading the color of both loose and mounted diamonds.

SUMMARY OF THE INVENTION

Accordingly, an object of the present invention is to provide a non-destructive and rapid examination method for the color-grading of diamonds.

To achieve the above-mentioned object, the method of diamond color grading comprises steps of: providing a Raman spectrometer operating with a laser beam of wavelength 785 nm and total laser energy of 450 mW for an average detection of surfaces of diamonds; six continuous scans being performed on each diamond to obtain an averaged Raman spectrum; a spectral range of the Raman spectrometer used for data acquisition being 100-3300 $cm^{-1}$; and each Raman spectrum being processed by background subtraction and peak intensity normalization so as to result in a smooth baseline and calibrated intensity, from which the diamond color is capable of being graded based on a characteristic peak at 2030 $cm^{-1}$.

DESCRIPTION OF THE PREFERRED EMBODIMENTS

To provide quantitative data for the color-grading of diamonds, the signal intensity of a characteristic peak at 2030 $cm^{-1}$ from the Raman spectra of diamond is used. The procedures comprises the technique are detailed below. A total of five GIA certified diamonds (with GIA Reports) with color ranging from E, F, H, K and L are examined as samples in the method of the present invention.

Throughout the experiment, the Raman spectrometer ProTT-EZRaman-A6 is used. The wavelength of the laser beam and the power used for the experiment are 785 nm and 450 mw, respectively. Using multi-mode laser specification, a laser spot covers a spatial resolution exceeding 100 μm on the surface of diamond, which allows a homogeneous sampling of the Raman signal.

Figure 1A:
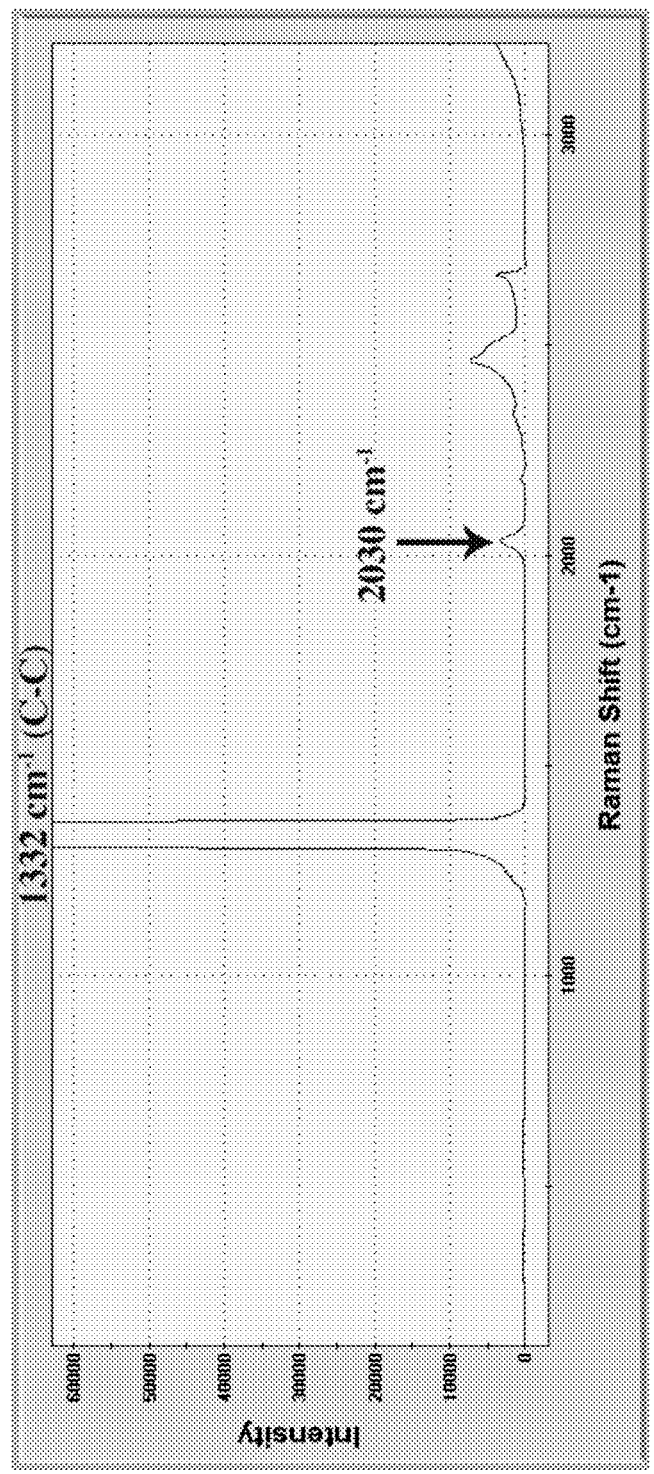
FIG. 1a shows a Raman spectrum of diamond in a spectral range of 100 $cm^{-1}$ to 3300 $cm^{-1}$.
Figure 1B:
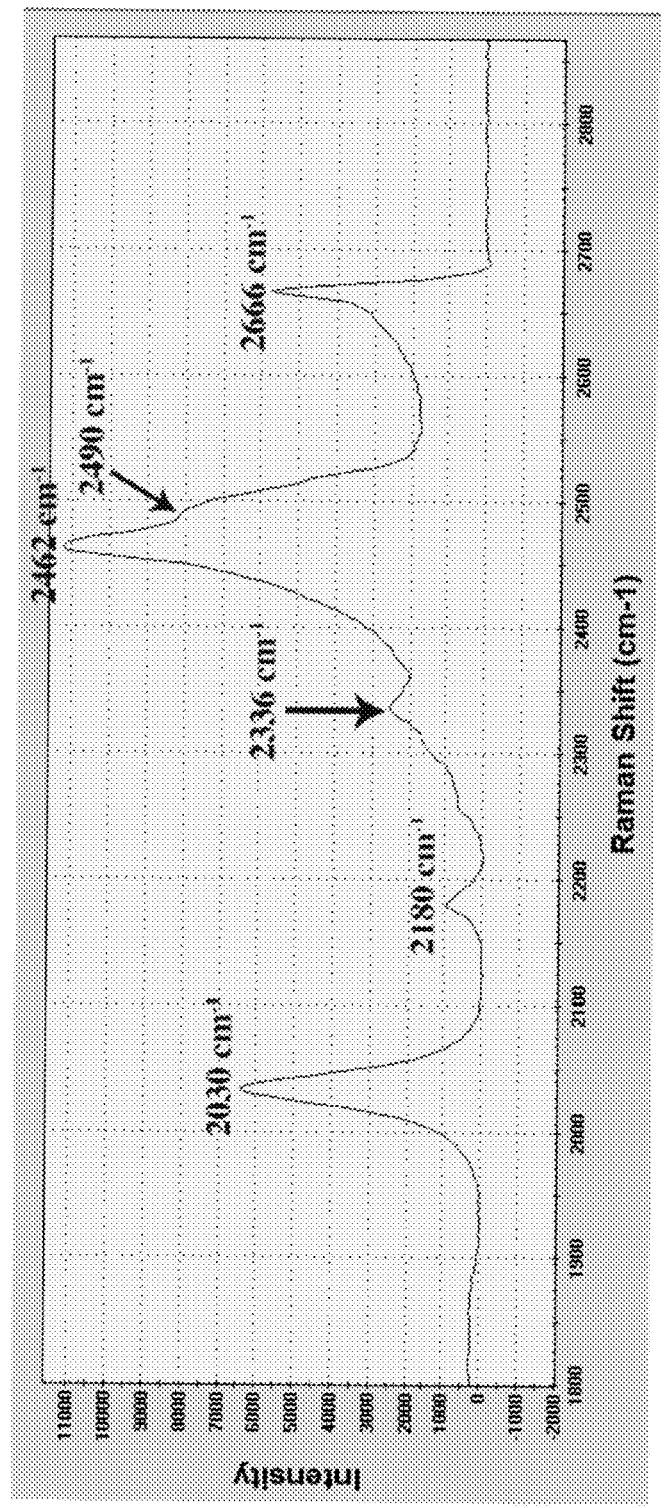
FIG. 1b shows Raman spectra of diamond in a spectral range of 1800 $cm^{-1}$~2800 $cm^{-1}$ illustrating second-order Raman modes of diamond (2180 $cm^{-1}$, 2336 $cm^{-1}$, 2462 $cm^{-1}$, 2490 $cm^{-1}$ and 2666 $cm^{-1}$) accompanying the 2030 $cm^{-1}$ peak. (Zoom in)

The spectral range of the spectrometer used for data acquisition is 100~3300 $cm^{-1}$. In each sample, six scans on different spots are performed to obtain an averaged Raman spectrum for further analysis. Each Raman spectrum is processed by background subtraction and peak intensity normalization through a specific program. This resulted in a Raman spectrogram with a smooth baseline and calibrated intensity (FIGS. 1a and 1b).

Figure 2A:
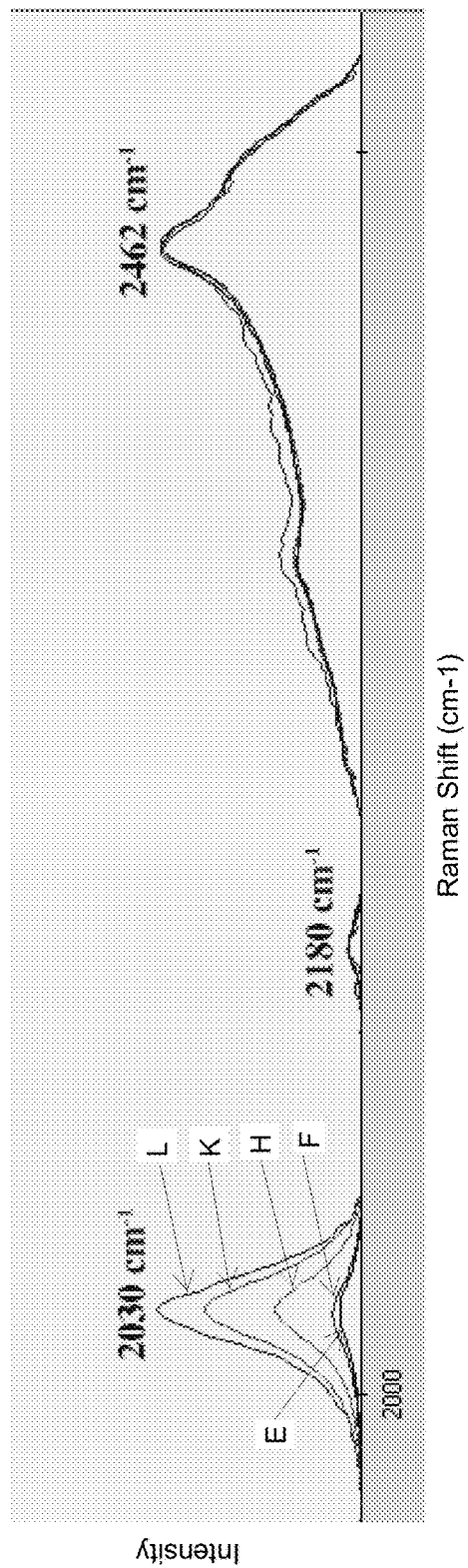
FIG. 2a shows Raman spectra of five samples overlaid after the normalized process in the spectral range of 1900 $cm^{-1}$~2700 $cm^{-1}$.

The Raman characteristic peak of an ordinary diamond, corresponding to the vibration mode of the C—C bond, is at 1332 $cm^{-1}$. However, instead of the C—C mode, another peak at 2030 $cm^{-1}$ (FIGS. 1a and 1b) is used as a clue for the color-grading of diamonds. In this study, it is noted that the intensity of the 2030 $cm^{-1}$ peak increases with the more yellowish tint of natural untreated diamonds. In each specimen, in order to be quantitative, normalization of intensity, i.e., by comparing the 2030 $cm^{-1}$ peak with a reference Raman mode, is required. The intensity of the 1332 $cm^{-1}$ peak is too high to be used as reference for the normalization of the intensity of 2030 $cm^{-1}$ peak. Instead, Some minor peaks in the Raman spectrum in spectral range between 1600 $cm^{-1}$ and 2800 $cm^{-1}$, with their intensity comparable to that of 2030 $cm^{-1}$ peak, are suitable for the normalized purpose (FIG. 2a). In FIG. 2a, a characteristic second-order Raman peak of diamond at 2462 $cm^{-1}$ which shows up invariantly accompanying the 2030 $cm^{-1}$ peak in each specimen, is used as reference for normalization.

Figure 2B:
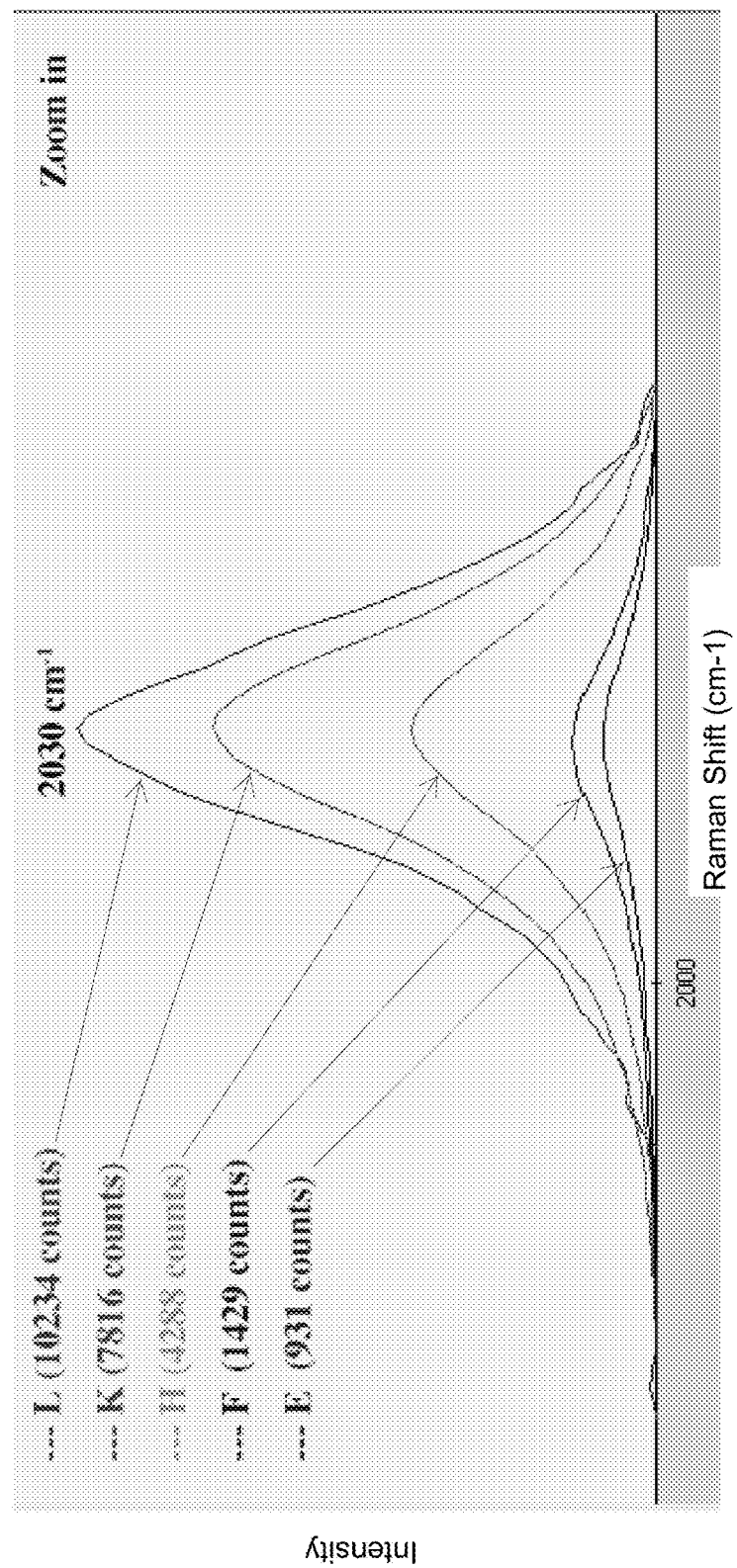
FIG. 2b shows Raman spectra of the five samples at the 2030 $cm^{-1}$ peak overlaid, showing that the intensity increases from 931 counts, 1429 counts, 4288 counts, 7816 counts and 10234 counts with the decrease in grade. (E→F-→H→K→L).

In the present research, the intensity of the 2030 $cm^{-1}$ peak, after being processed by normalization against the second-order Raman modes of diamond (more specifically, against the 2462 $cm^{-1}$ peak), exhibits a positive correlation with the yellowish tint of diamond (from colorless to yellowish white) and a negative correlation with their color-grades (FIG. 2a and FIG. 2b). In other words, the stronger intensity corresponds to a much deeper yellow color which represents a much lower grade of diamond.

To date, there is few research or analysis on the Raman peak of diamonds at 2030 $cm^{-1}$. The Raman peak of diamonds at 2030 $cm^{-1}$ is considered as the N-related bond due to the presence of nitrogen impurity in the natural untreated diamonds. It is reported that some C—N related compounds, such as Pb $(SCN)_2$, show C—N bonding vibration mode at ~2030 $cm^{-1}$.

As described above, it is clear that the use of the Raman spectra in the method of the present invention has the advantages of being non-destructive, no requirement for sample treatment and rapidity in analysis. Furthermore, it is based on scientific criterion. It may serve as a novel and semi-quantitative method in complementary to the conventional colorimetric method.

Accordingly, the main features of the method of the present invention are as follows: 1. after the correction and normalization, the Raman characteristic peak of diamonds at 2030 $cm^{-1}$ can be used to grade the diamond, and further provides quantitative data for a scientific, objective, orderly and auxiliary color-grading method; 2. the method of the present invention can be applied for the color grading of both loose and inlaid diamonds and for diamonds of all sizes.

It is understood that the invention may be embodied in other forms within the scope of the claims. Thus the present examples and embodiments are to be considered in all respects as illustrative, and not restrictive, of the invention defined by the claims.

What is claimed is:

1. A method of a diamond color grading, comprising steps of:
   providing a Raman spectrometer operating with a laser beam of wavelength 785 nm and total laser energy of 450 mW for an average detection of surfaces of diamonds;
   six continuous scans being performed on each diamond to obtain an averaged Raman spectrum;
   a spectral range of the Raman spectrometer used for data acquisition being 100-3300 $cm^{-1}$; and
   each Raman spectrum being processed by background subtraction and peak intensity normalization so as to result in a smooth baseline and calibrated intensity, from which the diamond color is capable of being graded based on a characteristic peak at 2030 $cm^{-1}$ such that a stronger intensity corresponds to a much deeper yellow color which represents a much lower grade of diamond.

* * * * *